(12) United States Patent
Colson

(10) Patent No.: US 8,486,459 B2
(45) Date of Patent: Jul. 16, 2013

(54) BULBINE FRUTESCENS EXTRACT

(75) Inventor: Michel Colson, Paris (FR)

(73) Assignee: Cremer Oleo GmbH & Co. KG, Hamburg (DE)

(*) Notice: Subject to any disclaimer, the term of this patent is extended or adjusted under 35 U.S.C. 154(b) by 135 days.

(21) Appl. No.: 13/106,175

(22) Filed: May 12, 2011

(65) Prior Publication Data

US 2011/0305785 A1   Dec. 15, 2011

(51) Int. Cl.
*A61K 36/00* (2006.01)

(52) U.S. Cl.
USPC .......................................... 424/725; 424/774

(58) Field of Classification Search
None
See application file for complete search history.

(56) References Cited

U.S. PATENT DOCUMENTS

| | | | |
|---|---|---|---|
| 3,892,853 A | 7/1975 | Cobble | |
| 4,178,372 A | 12/1979 | Coats | |
| 6,159,494 A | 12/2000 | Widgerow et al. | |
| 2010/0062085 A1 | 3/2010 | Widgerow | |

OTHER PUBLICATIONS

Van Staden et al., Knipholone From Bulbine Latifolia and Bulbine Frutescens, Phytochemistry, vol. 35, pp. 685-686 (1994).
Dagne et al., Knipholone: A Unique Anthraquinone Derivative from Kniphofia Foliosa, Phytochemistry, vol. 23, pp. 1729-1731 (1984).
Dagne et al., New Bianthraquinone Pigments from Kniphofia Species, Bull. Chem. Soc. Ethlop., 1(1), pp. 32.35 (1987).
Ito et al., Chrysophanol Glycosides from Callus Cultures of *Monocotyledonous kniphofia* spp. (Asphodelaceae), Chem. Pharm. Bull., 52, pp. 1262-1264 (2004).
Abegaz et al., Gaboroquinines A and B and 4'-O-Demethylknipholone-4'-O-β-D-glucopyranoside, Phenylanthraquinones from the Roots of Bulbine frutescens, J. Nat. Prod. 65, pp. 1117-1121 (2002).
Govender et al., Traditional herbal medicines: microbial contamination, consumer safety and the need for standards, South African Journal of Science 102, pp. 253-255 (2006).
A. M. Showalter, Arabinogalactan-proteins: structure, expressionand function, Cell. Mol. Life Sci. 58, pp. 1399-1417 (2001).
Yamada et al., Complement-activating polysaccharides from medicinal herbs, Immunomodulatory Agents from Plants, pp. 161-202 (1999).
Benson, Transdermal Drug Delivery: Penetration Enhancement Techniques, Current Drug Delivery 2, pp. 23-33 (2005).
Rabe et al, Antibacterial activity of South African plants used for medicinal purposes, J. of Ethnopharmacology 56, pp. 81-87 (1997).
Widgerow, A. et al.; New Innovations in Scar Management. Aesth. Plast. Surg. 24 (2000), pp. 227-234.
Watt, J. M.; Breyer-Brandwijk. M. G.: The Medicinal and Poisonous Plants of Southern and Eastern Africa. 2nd Edition; Livingstone, 1962, pp. 695-696.
Kiepenkerl Gartenwelt Aktuell; May 2010.
Motsei et al.; Screening of traditionally used South African plants for antifungal activity against *Candida albicans*; J. of Ethnopharmacology 86 (2003); pp. 235-241.
Pather et al.; A biochemical comparison of the in vivo effects of Bulbine frutescens and Bulbine natalensis on cutaneous wound healing; J. of Ethnopharmacology 133 (2011); pp. 364-370.
Coopoosamy; Traditional information and antibacterial activity of four Bulbine species (Wolf); African J. of Biotechnology, vol. 10 (2), Jan. 2011, pp. 220-224.

*Primary Examiner* — Qiuwen Mi
(74) *Attorney, Agent, or Firm* — Porter, Wright, Morris & Arthur LLP

(57) ABSTRACT

A method of producing a *Bulbine frutescens* extract in a stable form by treating juice expressed from the leaves of the *Bulbine frutescens* plant with hydrogen peroxide, removing the remaining hydrogen peroxide and stabilizing the extract using a suitable stabilizer. The *Bulbine frutescens* extract is used in the therapeutic or cosmetic fields and has an especially good effect on diseases of the skin and mucous membranes, in particular infections or inflammations such as fungal diseases, in prevention and/or curing injuries to the skin and mucous membranes, in particular burn wounds, as a disinfectant, as an agent to improve the immune defense, for body care, oral care, as an antiperspirants and as an antiaging product. The effect is to some extent far superior to that of commercial products, and there is no damage to the natural microflora of the skin and mucous membranes but instead they remain intact. Furthermore, the appearance of the skin is greatly improved.

10 Claims, No Drawings

BULBINE FRUTESCENS EXTRACT

BACKGROUND

The invention relates to a *Bulbine frutescens* extract, a method of manufacturing same, use of same in the medical and cosmetic fields and compositions comprising the inventive extract.

*Bulbine frutescens* (L.), which belongs to the family of Asphodelaceae/Liliaceae, is also known by the terms "Rankkopieva", "Ibhucu" or "Ithethe elimpofu". The German name is "stalked bulbine." This plant is widespread in South Africa, where more than 40 subspecies are known. It grows preferentially in sandy soil. The plant has a root stalk with numerous wiry roots; the leaves are 15 cm long and 4 to 8 mm thick, of a light green color and are fleshy and without hair. From April to August the plant bears yellow, orange or white blossoms in dense elongated flower clusters with a length of up to 30 cm and with a bearded stamen.

It is known that a gelatinous fluid obtained by expressing the leaves is used as an all-purpose curative against burns, abrasion wounds, damaged skin, skin rashes, eczema and ringworms, for example. The juice is expressed from a freshly picked leaf and applied to the area of skin affected. A tea infusion prepared from the fresh leaves is also known and is alleged to be helpful against colds, coughs, arthritis, diarrhea, bladder infections, infections of the urinary tract and some sexually transmissible diseases. However, the efficacy of this preparation has not yet been proven clinically nor have any professional reports about this been published.

Regarding the chemical composition of the fluid expressed from the leaves of plants in the *Bulbine* genus, however, some information is available. For example, Van Staden (Phytochemistry 35, 685 (1994)) has reported that knipholone is present in *Bulbine latifolia* and *Bulbine frutescens*. Knipholone is derived from 1,8 dihydroxyanthraquinone; it has a methyl group in position 3 and a 2,6 dihydroxy 4 methoxy 3 acetylphenyl group in position 4, also known as 2 acetyl-phloroglucine methyl ether group. Isoknipholone has the 2-acetylphloroglucine methyl ether group in position 9. 1,8 Dihydroxy 3 methylanthraquinone is better known as chrysophanol.

The occurrence of knipholone and its derivatives is limited practically to the *Bulbine* species although anthraquinones occur widely in nature. Knipholone also has been found in *Kniphofia* species, such as those described by Dagne and Steglich (Phytochemistry 23, 1729 (1984) and Bull. Chem. Soc. Ethlop. 32 1 (1987)). Leistner et al. (Chem. Pharm. Bull. 52, 1262 (2004)) have described knipholone derivatives in *Kniphofia foliosa* and *Kniphofla tuckii*, which are native to Ethiopia, with an emphasis on the glucose and disaccharide gentiobiose as the glucosidic part of these water-soluble anthraquinones.

Since the first report about knipholone in representatives of the Asphodelaceae family, a number of other aryl-substituted chrysophanol derivatives have been described either as glycosides or aglycones. Bringmann et al. (J. Nat. Prod. 65, 1117 (2002)) have described gaboroquinone A and B, 4'-O-demethylknipholone-4'-O-β-d-glucopyranoie and phenyl anthraquinones from the roots of *Bulbine frutescens*. Some of these compounds have exhibited moderate to good antiplasmoidal and antitrypanosomal effects in vitro. Bringmann et al. (2007) also found dimeric knipholone derivatives (joziknipholone A and B) in the roots of *Bulbine frutescens*. These joziknipholones have exhibited an effect in vitro against the chloroquine-resistant strain K1 of the malaria pathogen *Plasmodium falciparum* and a moderate effect against L5178Y leukemia lymphoma mouse cells.

Rabe and Van Staden (J. Ethnopharmacology 56, 81 (1997)) have investigated the in vitro effect of dried extracts from the leaves of *Bulbine frutescens* for their microbiological effect against *Staphylococcus aureus, Staphylococcus epidermidis* and *Bacillus subtilis*. However, these extracts have proven to be ineffective. Van Staden and Drewes tested knipholone in vitro for its antimicrobial effect against *Escherichia coli, Pseudomonas aeruginosa, Staphylococcus aureus, Bacillus subtilis, Micrococcus luteus* and *Candida albicans*, but these also proved ineffective. No reports about the bioavailability of *Bulbine frutescens* have been published.

Substituted 1,8-dihydroxyanthraquinones have also been found in various species of aloe such as *Aloe barbadensis, Aloe ferox* (which also belong to the Asphodelaceae family) and species of rhubarb such as *Rheum rhabarbarum* and *Rheum palmatum* (Chinese rhubarb). The anthraquinones in the aloe and rhubarb species lack the 2 acetylphloroglucine methyl ether group which is present in knipholone. The methyl group in position 3 may also be present in an oxidized form, either as the hydroxymethyl group, as an aldehyde or as an acid. The anthraquinones in aloe and rhubarb species are present as glycosides. The sugar radicals may be pentoses and/or hexoses. These are readily water soluble but after aging of these extracts or excessive heating, hydrolysis may occur and the anthraquinones become insoluble in water.

The anthraquinones present in *Bulbine* species have a completely different physiological potential than the anthraquinones originating from species of aloe and rhubarb. The anthraquinones from aloe and rhubarb species often have laxative properties. In 1987, the fundamental compound 1,8 dihydroxyanthraquinone (Danthron®) was taken off the market throughout the world because of the well-founded suspicion that this compound is carcinogenic for humans. However, toxic adverse effects such as those with aloe/rhubarb anthraquinones essentially do not occur with knipholone anthraquinones. Therefore, the manufacturers of aloe gels make a great effort to reduce the anthraquinones component as much as possible because it is mainly the polysaccharide component that is important in aloe gels.

There is thus a demand for supplying additional means for various therapeutic purposes and other means which have an improved and verifiable spectrum of effects in comparison with known compounds, that can be used in various fields and are easily obtainable and applicable. While a variety of compositions and methods have been made and used, it is believed that no one prior to the inventor has made or used an invention as described herein.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various examples of compositions including the *Bulbine frutescens* extract are described herein, the *Bulbine frutescens* extract may be formulated into a variety of other compositions which include various pharmaceutically and/or cosmetically-acceptable ingredients other than, or in addition to, those described herein. Accordingly, the descriptions should be regarded as illustrative in nature and not restrictive.

The present invention relates to a *Bulbine frutescens* extract, a method for producing a *Bulbine frutescens* extract, and use of a *Bulbine frutescens* extract in the medical or cosmetic field, or as a disinfectant. Some embodiments described herein are pharmaceutical or cosmetic compositions comprising the extract. The extract described herein may be used in the medical field, for example, in the treatment of diseases of the skin or mucous membranes, such as those associated with a microbiological cause, for example, due to opportunistic microorganisms or hypo/hyperactive enzymes. In the cosmetic field the extract may be used for body care, for example. The extract also serves to strengthen the immune system and therefore is especially suitable for treatment of persons with a weakened immune system.

The extract may be obtained by treating the juice obtained from *Bulbine frutescens* leaves with peroxide (particularly, hydrogen peroxide), and thereafter at least partially destroying the peroxide with one or more acids so as to produce a *Bulbine frutescens* extract. By way of example, a *Bulbine frutescens* extract may be produced by the following steps:

(1) Treating gelatinous juice expressed from *Bulbine frutescens* leaves with hydrogen peroxide while stirring, adding 0.5 to 20 g hydrogen peroxide per kg of the juice;

(2) Destroying the hydrogen peroxide by adding one or more pharmaceutically or cosmetically acceptable acids while stirring until the peroxide value of the solution is less than 0.02 meq O/kg;

(3) Adjusting the pH to 3.0 to 4.0 by adding, as necessary, one or more pharmaceutically or cosmetically acceptable acids; and (4) Obtaining the extract while stirring as soon as all the components are dissolved.

The starting material from the *Bulbine frutescens* leaves may be obtained in a variety of ways. For example, harvested leaves may be washed with water, and optionally cut into smaller pieces. Thereafter the gelatinous juice may be expressed (e.g., squeezed out) from the leaves in ways known to those skilled in the art.

The leaves of *Bulbine frutescens* can be harvested throughout the entire year, but the harvest is usually conducted at least twice. It is expedient to quickly process the leaves further directly after harvesting them. After harvest, the leaves may be washed with water to remove dirt and soil. The gelatinous juice is then expressed from the leaves using suitable equipment. If necessary the leaves may be cut into smaller pieces to facilitate expression of the juice. The gelatinous juice thereby obtained is almost colorless, with a slightly yellowish coloration, and resembles a gel. In other words, it is viscous to slightly viscous, with the viscosity depending on the time of harvest and the age of the plant, among other factors.

The juice thereby obtained is then treated with hydrogen peroxide while being stirred. A planetary mixer may advantageously be used for this purpose. However any other stirrers may also be used. In any case good and thorough mixing should be ensured.

In one embodiment, the juice is mixed with a quantity of hydrogen peroxide such that 0.5 to 20 g hydrogen peroxide, calculated as $H_2O_2$, is used per kilogram of the juice. The precise amount depends on, among other things, the time of harvest and the age of the harvested plants. The hydrogen peroxide destroys the gel structure which originates from branched polysaccharides, and also denatures enzymes that are present. It has been observed that enzyme residues have a negative effect because they lead to increased coloration and to glycolysis of the knipholone glycosides and their derivatives. The duration of hydrogen peroxide treatment is not particularly limited, but it may be desirable to adjust the treatment time to be as short as possible in order to avoid oxidative side reactions which would lead to discoloration. Therefore, the hydrogen peroxide treatment time may be selected so that it does not result in any discoloration. For example, a treatment time of a few minutes up to 1 hour may be employed, or even a few minutes up to approximately half an hour. In one particular embodiment, the juice and hydrogen peroxide are stirred for 5 to 20 minutes. Although some previously unidentified oxidation processes may occur, leading to unwanted discoloration and to glycolysis of the knipholone glycosides, this can be reduced to a minimum by careful monitoring and limiting the treatment time.

Following hydrogen peroxide treatment of the expressed juice, the remaining hydrogen peroxide is destroyed by adding one or more pharmaceutically or cosmetically acceptable acids. The term "pharmaceutically or cosmetically acceptable" generally refers to compounds which can be used in the compositions and treatments described herein, are not undesirable from a medical or cosmetic standpoint, and which do not have any significant deleterious and/or harmful effect when in contact with the skin or mucous membranes as part of a medical or cosmetic treatment in the quantities contemplated herein (e.g., do not cause significant irritation, allergies or other problems in the user in consideration of the severity of the impairment or disease and the need for treatment). Pharmaceutically or cosmetically acceptable acids are selected, for example, from organic acids. Examples that can be mentioned include adipic acid, alginic acid, ascorbic acid, isoascorbic acid (erythorbic acid), aspartic acid, benzenesulfonic acid, succinic acid, 2-acetoxybenzoic acid, camphoric acid, camphorsulfonic acid, cinnamic acid, citric acid, in particular citric acid monohydrate, digluconic acid, ethanesulfonic acid, glutamic acid, glycolic acid, heptanoic acid, hexanoic acid, fumaric acid, 2-hydroxyethanesulfonic acid (isethionic acid), lactic acid, maleic acid, hydroxymaleic acid, malic acid, malonic acid, mandelic acid, pamoic acid, pectic acid, phenylacetic acid, 3-phenylpropionic acid, picric acid, pivalic acid, pyruvic acid, stearic acid, sulfanilic acid, tartaric acid, p-toluenesulfonic acid and the like.

Ascorbic acid and isoascorbic acid (erythorbic acid) are two particular acids suitable for destroying hydrogen peroxide in the methods described herein. Mixtures of two or more pharmaceutically or cosmetically acceptable acids may of course also be used.

After the addition of the pharmaceutically or cosmetically acceptable acid, for example, ascorbic acid or isoascorbic acid, the peroxide values may be less than 0.02 meq O/kg.

Next, the pH of the solution is adjusted to 3.0 to 4.0 with the addition (as necessary) of one more pharmaceutically or cosmetically acceptable acids. One of the acids described above may be used for this purpose, and it may be the same as or different from the acid(s) used to destroy the hydrogen peroxide. By way of example, citric acid monohydrate may be used to adjust the pH.

The extract end product is obtained by continuing to stir until all of the components are completely dissolved and no aggregates are present any longer. The stifling may be performed with any stirring device, such as a planetary stirrer.

The microbiological condition and the presence of pathogenic microorganisms in the extract end product may be controlled according to the methods described in the various pharmacopoeias such as the European Pharmacopoeia and/or the United States Pharmacopoeia such that the aerobic microbe count is less than 100 CFU/g, or even 10 CFU/g or less. Like any material for medicinal or cosmetic use, it is desirable that essentially no pathogens are present. The desired microbial freedom and freedom from pathogens can be achieved, for example, by working under sterile conditions, with sterile equipment, and using controlled starting materials.

It may also be desirable to protect the *Bulbine frutescens* extract that is prepared from opportunistic microorganisms. For example, Govender, du Plessis-Stoman, Downing and Van De Venter (South African Journal of Science 102, 253 (2006)) came to the conclusion that many products offered in the local markets were microbially contaminated and should be considered a health risk for humans.

Therefore, one or more pharmaceutically or cosmetically acceptable preservatives may be added to the *Bulbine frutescens* extract. Pharmaceutically or cosmetically acceptable preservatives include, for example, benzoic acid, sorbic acid, parabens (e.g., methyl, ethyl, propyl, butyl, isobutyl or benzyl paraben), formic acid, acetic acid, propionic acid, salicylic acid, p-anisic acid, levulinic acid, water-soluble salts of any of the foregoing, glycerol and polyglycerol monoesters of caprylic acid, capric acid lauric esters, diols such as 1,2 dihydroxypentane, 1,2 dihydroxyhexane, 1,2-dihydroxyoctane, 1-(2-ethylhexyl)glyceryl ether and the like. Mixtures of two or more preservatives may also be used.

The *Bulbine frutescens* extract may be used as described above, or it may be subjected to further processing. Further processing may be selected from one or more of the following procedures which may also be combined in any order: filtering, evaporation of water under reduced pressure/elevated temperature, azeotropic distillation under reduced pressure/elevated temperature using a suitable cosolvent, spray drying or freeze drying. The disadvantage of methods under an elevated temperature lies in the risk of conversion of the anthraquinones glycosides to the corresponding aglycones which are sparingly soluble/insoluble in water and thus reduce the effect of the *Bulbine frutescens* extract. Freeze drying has the advantage that conversion of anthraquinones glycosides to the corresponding aglycones is greatly inhibited. The presence of aglycones can be tested, for example, by dissolving the insoluble portion in acetone/DMSO and then adding potassium hydroxide. An intense red/magenta/violet coloration appears.

The *Bulbine frutescens* extract obtained by the peroxide-treatment of the juice expressed from *Bulbine frutescens* leaves has been shown to have a variety of uses in both the therapeutic and cosmetic fields.

Use in the cosmetic field includes body care and beauty care, in other words, maintenance, restoration or improving the beauty of the human body, for example, by cleaning, stabilizing, moisturizing, vitalizing and/or deodorizing the skin and cleaning, stabilizing and/or vitalizing the mucous membranes.

The use in the therapeutic field comprises, for example, application of the *Bulbine frutescens* extract for treatment or prevention of diseases and injuries of the skin and mucous membranes. Diseases of the hair and nails, as well as of the sebaceous and sudoriferous glands, are also classified with the skin diseases because they are also of epidermal origin.

By way of example, publications in the literature have pointed out that essentially no antimicrobial properties are present in *Bulbine frutescens*. It has now surprisingly been found that the *Bulbine frutescens* extract described herein has unexpected antimicrobial properties. The experiments described below in the experimental part have yielded results that are extremely surprising, completely unexpected and in contradiction with previous information published in the literature. The proven antimicrobial properties of the *Bulbine frutescens* extract make it possible to provide products with advantages with regard to special antimicrobial requirements. These experiments have also shown that, although the *Bulbine frutescens* extract described herein may not, by itself, always achieve complete destruction of all microorganisms, it is a functional ingredient which provides unexpected antimicrobial effects. Thus, for example, the *Bulbine frutescens* extract may be incorporated into a variety of antimicrobial compositions along with one or more additional antimicrobial agents, and optionally along with other therapeutic agents. Such antimicrobial compositions may further include pharmaceutically-acceptable excipients and other additives (e.g., colorants, fragrances, preservatives, etc.) known to those skilled in the art. These compositions may be formulated in a variety of forms, such as those suitable for application to the skin and/or mucous membranes, or even other forms appropriate for the intended use (e.g., as a disinfecting spray for use on inanimate surfaces).

By way of specific example, additional experiments have shown that the *Bulbine frutescens* extract, when enriched with a small amount of hydrogen peroxide (for example, adding 0.05 wt % to the extract, expressed as $H_2O_2$) acts as a disinfectant against certain microorganisms. For example, peroxide enriched *Bulbine frutescens* extract has been shown to be effective against *Staphylococcus aureus*, including methicillin-resistant *Staphylococcus aureus* (MRSA) and clindamycin, erythromycin and ciprofloxacin-resistant *Staphylococcus aureus* (CEC SA). These resistant strains are usually difficult to control, in particular in a hospital environment. Tests have also shown that many other desirable microorganisms are not affected by the composition described herein or are affected only to a limited extent, including in particular the natural microflora of the skin and mucous membranes, such that the natural microflora of the skin and mucous membranes can be protected. Therefore, the *Bulbine frutescens* extract described herein, in particular when enriched with a small amount of hydrogen peroxide (for example, 0.05 wt %, expressed as $H_2O_2$), is suitable for disinfecting inanimate surfaces such as those found in hospitals (e.g., operating rooms), doctor's offices, athletic facilities (e.g., locker rooms), etc. For such uses, the peroxide-enriched extract can be formulated as a liquid suitable for spray application (e.g., a solution comprising the peroxide-enriched extract and water), impregnated wipes, concentrated solutions which are diluted prior to use (e.g., with water), or any of a variety of other appropriate forms known to those skilled in the art.

Comparative experiments in which hydrogen peroxide (for example, 0.05 wt %, expressed as $H_2O_2$) was tested alone did not yield the antimicrobial properties provided by *Bulbine frutescens* extract enriched with hydrogen peroxide (for example, 0.05 wt % expressed as $H_2O_2$). In addition, the antimicrobial effect of the peroxide enriched extract exceeded the expected performance based on the individual antimicrobial effects of $H_2O_2$ and the extract by themselves. Thus, the addition of hydrogen peroxide to the *Bulbine frutescens* extract, such as up to 0.1 wt % $H_2O_2$ added to the extract, provides a surprising synergistic effect.

The *Bulbine frutescens* extract consists of many different chemical units, including polysaccharides. Since some polysaccharides have proven beneficial in wound healing, in vitro studies were conducted to determine the cytotoxicity and cell proliferation effects of the *Bulbine frutescens* extract. The extract does not have any cytotoxic properties and cell division was better than 100% at 0.1 µg/mL. In addition, it has been found that the *Bulbine frutescens* extract has a particularly strong wound-healing effect on injuries to the skin and mucous membranes. Biochemical analyses of wound tissue treated with the *Bulbine frutescens* extract have shown a definitely elevated quantity of collagen, protein and total DNA content in comparison with untreated wounds. Wound incisions in porcine skin have shown a greatly elevated increase in wound closure and a complete re-epithelialization in comparison with untreated wounds. A good wound treatment is important because clinical infections may occur if the bacterial colonies increase to a critical extent in and around the wound locations. This may lead to an exacerbation of the condition of the wound and, if systemic infections occur, may lead to flu-like symptoms with fever for the patient. Systemic antibiotics are often necessary and are an essential component of treatment. With early treatment with the *Bulbine frutescens* extract, it may not be necessary to administer antibiotics because of the favorable course of wound healing.

The *Bulbine frutescens* extract may also be used as a prophylactic agent to prevent wounds, for example, burns, or to facilitate healing of burns. The *Bulbine frutescens* extract can also be used especially successfully in healing of small wounds such as those which occur with shaving and in removal of hair and ingrown hairs in men with very kinky hair, on poorly healing wounds, for example, caused by an infection due to methicillin-resistant *Staphylococcus aureus* (MRSA) and clindamycin, erythromycin and ciprofloxacin-resistant *Staphylococcus aureus* (CEC SA) (especially on the feet) and also on small wounds.

The *Bulbine frutescens* extract has also proven successful in the treatment of furuncles and carbuncles.

It is also assumed that arabinogalactans (AGs) are the most important polysaccharides. These polysaccharides are composed of arabinose and galactose (monosaccharides). Arabinogalactans are produced by plants. Arabinogalactans are present in large quantities in gum Arabic and gum ghatti, for example. Furthermore, certain microorganisms produce arabinogalactans. Arabinogalactan proteins (AGPs) function as signal molecules between the cells and as an adhesive for closing wounds on plants. Arabinogalactans are known to stimulate the immune system of plants because they increase the activity of natural killer cells and other components of the immune system (A. M. Showalter, Cell. Mol. Life Sci. 58, 1399 (2001)). Although this is true of plants in particular, they can also support the human body in fighting infections, as proposed by Yamada and Kiyohara ("Complement-activating polysaccharides from medicinal herbs", Immunomodulatory Agents from Plants, 161-202 (1999), H. Wagner (ed.), Birkäuser Basel).

Experiments have now shown that the *Bulbine frutescens* extract actually has highly immune strengthening properties. This is proven by experiments in which the *Bulbine frutescens* extract resulted in wound healing of immunologically weakened people, in particular in patients with type 2 diabetes with poor wound healing on the feet and the lower extremities. Wound healing was also achieved even on wounds that had already been in existence for a long time by using the extract described herein, although to some extent also including the formation of a scar. The *Bulbine frutescens* extract can therefore also be used in wound healing of poorly healing wounds, for example, in patients with type 2 diabetes or in AIDS patients.

Thus, the *Bulbine frutescens* extract may be used as an agent for strengthening the immunological system. Due to the combination effect of the *Bulbine frutescens* extract, which also has immunomodulating effects in addition to curative effects, the *Bulbine frutescens* extract may be used especially successfully for prevention/prophylaxis and rapid healing.

The *Bulbine frutescens* extract may also be used effectively to combat fungus infections of the nails and feet. Fungus infections of the nails and feet are caused by fungi. Infections due to anthropophilic pathogens, for example, *Trichophyton rubrum* are usually less intense but are more chronic than infections with zoophilic pathogens such as *Trichophyton mentagrophytes*. These microorganisms are easily transmissible by direct or indirect contact with infected persons. These microorganisms are usually difficult to eliminate because they settle not only on the surface of the skin or nails but are also present in the subcutaneous tissue. Most fungicides such as clotrimazole, terbinafine and miconazole have only a very restricted depth of penetration, which results in a high incidence of relapses. The efficacy of these agents is therefore very restricted.

However, the *Bulbine frutescens* extract unexpectedly strengthens the transdermal transport (even in nails), as demonstrated by tests with the Franz diffusion cell. Furthermore, the transdermal transport can be further improved by using a penetration enhancer such as polysorbate 80, unsaturated phosphatidylcholine and similar phospholipids, phytantriol and other products as described by Benson (Current Drug Delivery 2, 23 (2005)), for example.

The *Bulbine frutescens* extract has also been used successfully against candidiasis. The yeast *Candida albicans* and related species are responsible for various types of candidiasis, for example, topical or vaginal candidiasis. Treatment with traditional pharmaceutical products leads to a high incidence of relapses, in particular in patients with a weakened immune system. *Candida albicans* can be treated effectively with the *Bulbine frutescens* extract.

Thus, the *Bulbine frutescens* extract described herein may be used to produce a pharmaceutical composition for the treatment of diseases of the skin or mucous membranes, such as infections or inflammations of the skin or mucous membranes including fungal diseases, as well as pharmaceutical compositions for the treatment or prevention of injuries to the skin or mucous membranes such as burns and other wounds.

It should also be noted that the phrase "*Bulbine frutescens* extract" or "extract" as used in herein is not necessarily limited to particular forms of administration or formulations. Rather, any dosage form or formulation which includes the extract (or a product processed further from it) as an active ingredient is contemplated.

In addition to a wide variety of therapeutic uses, it has been found that the *Bulbine frutescens* extract may also be used for body care as well as other cosmetic uses. For example, the extract provides a highly active agent in antiperspirant and/or deodorant compositions. (As used herein, the term "antiperspirant" includes compositions intended to prevent perspiration, as well as those intended to prevent odor due to perspiration.) Human perspiration is odorless immediately after secretion but the sterol esters present in perspiration are subject to microbial hydrolysis which forms not only short chain carboxylic acids (acetic acid, baldrianic acid, butyric acid and isobutyric acid) but also androstenes. Androstenes and short-chain carboxylic acids are responsible for the perceptible unpleasant odor. The microorganisms responsible for the hydrolysis of androstene esters are often attributed to the family of Lactobacillaceae, lactic acid producing microorganisms, but may also be other gram-positive or gram-negative bacteria such as *Staphylococcus epidermides*. By reducing or eliminating these microorganisms, the unpleasant odor can be reduced or completely eliminated. Conventional antiperspirant formulations to which the *Bulbine frutescens* extract has been added are especially effective. The efficacy of such formulations is further improved by building up a skin barrier.

Another area for application of the *Bulbine frutescens* extract is in oral care. It has recently been found that a disturbed oral microflora can cause cardiovascular diseases and miscarriages. The *Bulbine frutescens* extract makes an extremely effective contribution in regulating oral microflora, where the mouth odor can serve as a measure of efficacy. In some cases, hydrogen sulfide, methyl mercaptan and dimethyl sulfide make a significant contribution to mouth odor in addition to various alkylated amines. Experiments have shown that by rinsing the mouth with a 10% aqueous solution of *Bulbine frutescens* extract, unpleasant mouth odor can be eliminated completely. Minor infections and inflammations of the gingiva and the oral mucosa disappear. The *Bulbine frutescens* extract is thus superior to traditional pharmaceutical preparations, including preparations for oral disinfection based on chlorhexidine gluconate and hydrogen peroxide. *S. salivarius* is hardly impaired by *Bulbine frutescens* extract, while chlorhexidine and hydrogen peroxide are strongly damaging for the commensal microflora in the oral cavity.

As already described, the *Bulbine frutescens* extract strengthens the immune system, which is presumably attributable mainly to the polysaccharides it contains. Another related application is the use of the extract in antiaging products. The important thing here is that it has a positive effect on the elasticity of skin, for example, the strength of skin, the water balance of the skin and cell differentiation and cell proliferation. Experiments have shown that the *Bulbine frutescens* extract, formulated as a cream for example, leads to a definitely improved elasticity and a significantly improved strength of the skin, while at the same time greatly reducing the water loss of the subcutaneous tissue. A definitely improved visual presentation of the skin has also been observed.

As mentioned previously, cosmetic or pharmaceutical compositions comprising the *Bulbine frutescens* extract may also include one or more pharmaceutically or cosmetically acceptable vehicles or excipients. Those skilled in the art are familiar with pharmaceutically or cosmetically acceptable vehicles and excipients. These vehicles and excipients include, for example, ion exchangers, emulsifiers, binders, suspension aids, stabilizers, bacteriostatic agents, antioxidants, lecithin, serum proteins, buffer substances, pH regulating agents, preservatives, water, salts and/or electrolytes, substances based on cellulose, and numerous other cosmetically or pharmaceutically acceptable additives.

For therapeutic or cosmetic use, the extract may be applied to the skin or mucous membranes in any traditional dosage form and in any traditional manner. Preferred administration pathways include transdermally and topically. The dosage of the *Bulbine frutescens* extract depends on, among other things, the dosage form, the intended purpose, the impairment to be treated, the disease or disorder, the user, the specifically selected vehicles and/or excipients. The extract may be administered in the selected dosage form and/or formulation, such as through external topical application. The dosage form and/or formulations may therefore be selected and adjusted for transdermal or topical administration. Such formulations may be prepared as a liquid, solid or semisolid dosage form. Examples include drops, tinctures, oils, rinsing solutions, suspensions, emulsions, creams, lotions, milks, ointments, jellies, viscous liquids, shake mixtures, powders, pastes, sprays, transdermal patches, or other forms known to those skilled in the art.

The advantages of the *Bulbine frutescens* extract described herein, and compositions which include such extract, are extremely varied:

The *Bulbine frutescens* extract is obtained by the peroxide treatment of juice expressed from the leaves of *Bulbine frutescens*. After removal of all or most of the remaining peroxide, the a suitable stabilizer (e.g., one or more preservatives) may be added to the extract. The resulting extract can be formulated as is or it may be subjected to a suitable further processing and then incorporated into a suitable formulation form.

The extract may be used in the cosmetic and therapeutic fields. The dosage form is not limited, and the extract in the selected formulation is expediently applied topically to the area to be treated. The usual route of administration is transdermal or topical, where the formulation containing the extract is applied locally to the skin and/or mucous membranes.

It has been found in a completely unexpected manner that the *Bulbine frutescens* extract has antimicrobial properties. The *Bulbine frutescens* extract, particularly when enriched with a small amount of hydrogen peroxide (for example, 0.05 wt %, expressed as $H_2O_2$), may even be used as a disinfectant. Such a combination disinfectant is even effective against *Staphylococcus aureus* including methicillin-resistant *Staphylococcus aureus* (MRSA) and clindamycin, erythromycin and ciprofloxacin-resistant *Staphylococcus aureus* (CECSA).

The *Bulbine frutescens* extract can be used advantageously for therapeutic treatment of infections and diseases of the skin and mucous membranes. This includes fungal diseases such as fungus infections of the feet and nails or candidiasis (including topical and vaginal candidiasis), injuries to the skin and mucous membranes such as burns and other types of wounds, and even furuncles and carbuncles. The extract is also effective as a preventive, for example, to prevent injuries and/or wounds to the skin or mucous membranes.

The extract may also be administered to strengthen the immune system. This plays a role in particular in patients with a weakened immune system, for example, in diabetes or AIDS patients. Due to the combination effect of *Bulbine frutescens* extract which has both immunomodulating properties and healing effects, the *Bulbine frutescens* extract may be used especially successfully for prevention/prophylaxis and for rapid healing. Infections and inflammations subside within a short period of time, wounds heal much more rapidly and the immune system is strengthened so that relapses can be largely ruled out. In fact, the good wound healing achieved through the use of the *Bulbine frutescens* extract may prevent the need for additional administration of antibiotics.

In the cosmetic field, the extract may be used for body care, oral care, as an antiperspirant and as an antiaging product. The effect is to some extent far superior to that of commercial products, and the natural microflora of the skin and mucous membranes is not damaged but instead remains intact.

In particular applications in the cosmetic field, for example, as an antiaging product, the positive influence of the extract on the skin and mucous membranes is manifested. For example, the elasticity of the skin and the strength of the skin increases, while there is a long-lasting positive influence on the water balance of the skin as well as cell differentiation and cell proliferation. Furthermore, the appearance of the skin is definitely improved.

In the experimental part which follows, some experiments in which the therapeutic and cosmetic efficacy of the *Bulbine frutescens* extract are demonstrated and described in detail. The scope of the present invention should of course not be restricted to these particular examples.

Experiments in Microbiological Investigation and Evaluation of the *Bulbine frutescens* Extract The antimicrobial properties of the *Bulbine frutescens* extract were investigated. For this purpose, after appropriate processing of the leaves, treatment with hydrogen peroxide, elimination of the remaining hydrogen peroxide and stabilization at a suitable pH using a suitable stabilizer, the extract was obtained as already described in detail.

Kinetic Provocation Test 1

A kinetic provocation test was performed on various microorganisms using the *Bulbine frutescens* extract. The test was conducted in accordance with the method of the American Society for Testing and Materials (ASTM), method E1174. This test was performed in the presence of 0.1 wt % human serum with an inoculum of 106 CFU/g. After 6 hours the following logarithmic reductions were observed:

| | |
|---|---|
| *Clostridium perfringens*: | after 6 hours, no log reduction |
| *Clostridium tetani*: | after 6 hours no log reduction |
| *Streptococcus pyogenes* group A: | after 6 hours a 4 log reduction |
| *Staphylococcus aureus*: | after 6 hours a 6 log reduction (complete kill after 1 hour). |
| *Escherichia coli* O157H7: | after 6 hours a 6 log reduction (complete kill after 6 hours) |
| *Salmonella enteritidis* serotype Panama: | after 6 hours a 6 log reduction (complete kill after 6 hours) |
| *Candida albicans*: | after 6 hours a 1 log reduction |
| *Trichophyton mentagrophytes*: | after 6 hours a 2 log reduction |

The results were surprisingly good for a number of microorganisms and are in contrast with the results published in the literature.

Kinetic Provocation Test 2

In a second test the *Bulbine frutescens* extract was subjected to another kinetic provocation test but this time in the presence of 1 wt % human fecal matter. This test was also performed in accordance with the method of the American Society for Testing and Materials (ASTM) method E1174 using various inoculations. A testing period of two (2) hours was selected.

*Escherichia*, *Klebsiella* and *Enterobacter* species (aerobic gram-negative rods, Enterobacteriaceae): inoculation 105 CFU/g. Complete kill after 2 hours.

*Bacteroides* and *Fusobacterium* species (anaerobic gram-negative rods): inoculation 104 CFU/g. Complete kill after 1 hour.

*Staphylococcus* and *Streptococcus* species (aerobic gram-positive cocci): inoculation 104 CFU/g. Complete kill after 2 hours.

*Peptococcus* and *Peptostreptococcus* (anaerobic gram-positive cocci): inoculation 104 CFU/g. Complete kill after 1 hour.

*Lactobacillus* and *Bifidobacterium* (anaerobic gram-positive non-spore-forming rods): inoculation 104 CFU/g. Complete kill after 1 hour.

*Clostridium* species (anaerobic Gram-positive spore-forming rods): inoculation 102 FU/g. None were killed after 2 hours. After 24 hours, there was a 40% reduction.

*Candida albicans*: inoculation 102 CFU/g. Complete kill after 1 hour.

The results were again extremely surprising, completely unexpected and in contradiction with previous data published in the literature. These results show advantages with regard to special microbial requirements. The *Bulbine frutescens* extract can therefore be used as a functional ingredient.

Experiments in the Immunostimulating Properties of the *Bulbine frutescens* Extract Wound Healing in Patients with a Weakened Immune System Experiments were conducted in order to test the *Bulbine frutescens* extract in wound healing in immunologically weakened people, in particular, patients with type 2 diabetes and poor wound healing on the lower extremities (feet). Eight volunteers with nonhealing wounds an average of 11 cm² in size were selected. Four volunteers were given a placebo, and *Bulbine frutescens* extract was applied to the wounds of the other four. A definite improvement was observed in the volunteers treated with *Bulbine frutescens* extract: the wounds closed within 3 to 4 days. In the volunteers treated with the placebo preparation, no improvement was detected. Since the wounds had already been in existence for a long time, in one case more than a year, the development of discolored scar could not be prevented. Thus, the *Bulbine frutescens* extract can be used successfully in wound healing of poorly healing wounds, for example, in patients with type 2 diabetes.

Preventive Effect on Burn Wounds

Experiments were conducted to test the *Bulbine frutescens* extract on burns in cancer patients caused by irradiation with gamma rays. Irradiation with gamma rays is often used as a preventive measure following a surgical procedure, for example, after partial or complete mastectomy. Six patients with breast cancer were asked to apply the extract as a preventive measure to the body area that was to be exposed to gamma rays. After the irradiation program, no visible burn wounds were observed whereas the control group developed moderate to severe burn wounds. The *Bulbine frutescens* extract can therefore be used advantageously to prevent or treat burn wounds, such as those that occur during bombardment with gamma rays.

Experiments Using the *Bulbine frutescens* Extract in Cosmetics and for Treatment of the Skin Use of the *Bulbine frutescens* Extract as an Antiperspirant As already described, the extract was obtained after appropriate processing of the leaves of the plant, treatment thereof with hydrogen peroxide, removal of the remaining hydrogen peroxide and stabilization by using a suitable stabilizer. The extract was then incorporated into an antiperspirant formulation. One example of such a formulation is given below:

| | |
|---|---|
| Demineralized water | 82.1 wt % |
| Stearyl glucoside (emulsifier) | 4.2 wt % |
| *Bulbine frutescens* extract | 6.0 wt % |
| PPG-15 stearyl ether | 4.0 wt % |
| Decyl oleate | 1.5 wt % |
| Glycerol caprylate | 1.2 wt % |
| Hydroxyethyl cellulose | 0.4 wt % |
| Total | 100 wt % |

The pH of the formulation was 4.5 to 6.0.

The formulation obtained was slightly viscous and could be applied using a roll-on system for example. In one experiment (not optimized), an odor test was performed over a period of 8 hours in the form of a "sniff test." The formulation remained on the skin because of the choice of softeners used. Of course any other forms of administration with which the formulation can be applied to the skin are also possible, for example, in the form of a cream, lotion, spray, aerosol or in some other form. The *Bulbine frutescens* extract was especially effective for the axillary and genital areas. However it was not effective in the case of a trimethylaminuria syndrome.

Use of *Bulbine frutescens* Extract for Treatment of Nail Fungus and Athlete'S Foot The extract prepared as previously described was incorporated into the following topical formulation:

| | |
|---|---|
| Demineralized water | 82.6 wt % |
| *Bulbine frutescens* extract | 6.0 wt % |
| Pentylene glycol | 5.0 wt % |
| Unsaturated phosphatidylcholine | 4.0 wt % |
| Isononylisononanoate | 2.0 wt % |
| Hydroxyethyl cellulose | 0.4 wt % |
| Total | 100 wt % |

The pH of the formulation was 4.5 to 6.0.

The composition was applied to the feet of users with athlete's foot (six volunteers). It was found that the fungus microorganisms were completely eliminated after 35 days and no further relapses were observed after three months. The formulation did not have any negative effects on the commensal microflora of the skin. Consequently it has been shown that the *Bulbine frutescens* extract can be used effectively in the treatment of nail fungus and athlete's foot.

Use of *Bulbine frutescens* Extract in Oral Care Products

Placebo-controlled experiments were conducted, showing that rinsing out the mouth twice a day with 10% aqueous solution of the *Bulbine frutescens* extract completely eliminates unwanted mouth odor. At the same time it was observed that minor infections of the gingiva caused by *Streptococcus mutans* and/or *S. sanguis*, for example, can be regulated. Inflammation of the gingiva and the oral cavity treated with 10% aqueous *Bulbine frutescens* extract solution usually disappeared in 1 to 2 days which was thus superior to the traditional pharmaceutical preparations including preparations for oral disinfection based on chlorhexidine gluconate and hydrogen peroxide. *S. salivarius* was hardly impaired at all by the *Bulbine frutescens* extract. On the other hand chlorhexidine and hydrogen peroxide have an extremely harmful effect on the commensal microflora in the oral cavity. Thus, the *Bulbine frutescens* extract was effective to a great extent in oral care and is even superior to commercial products.

Use of *Bulbine frutescens* Extract in Antiaging Products

A cream containing the *Bulbine frutescens* extract having the following composition was tested for its antiaging properties:

| | |
|---|---|
| Demineralized water | 69.0 wt % |
| Ethyl hexyl stearate | 6.0 wt % |
| Cetearyl alcohol | 6.0 wt % |
| *Bulbine frutescens* extract | 6.0 wt % |
| Pentylene glycol | 5.0 wt % |
| Glycerol | 3.0 wt % |
| Ceteareth-6 | 2.5 wt % |
| Ceteareth-25 | 2.5 wt % |
| Total | 100 wt % |

The pH of the cream was 5.0 to 6.0.

The elasticity of the skin, the strength of the skin, the values of the corneometer measurement and the transepidermal water loss (TEWL) as well as the cell differentiation and cell proliferation were used as definite antiaging properties. Equipment from Courage and Khazaka Electronic GmbH, Cologne, Germany, was used to test the results. It was found that applying the cream twice daily led to a 40% improvement in elasticity and an approximately 24% improvement in tensile strength of the skin, and water loss of the subcutaneous tissue to the environment was greatly reduced in proportion to the standard.

Additional experiments have shown that cell metabolism is increasing by 15%. A visual inspection of the skin revealed that the appearance of the skin had improved significantly.

Use of *Bulbine frutescens* Extract in Topical Candidiasis

A cream containing the following was prepared:

| | |
|---|---|
| Demineralized water | 69.0 wt % |
| Ethyl hexyl stearate | 6.0 wt % |
| Cetearyl alcohol | 6.0 wt % |
| *Bulbine frutescens* extract | 6.0 wt % |
| Pentylene glycol | 5.0 wt % |
| Glycerol | 3.0 wt % |
| Ceteareth-6 | 2.5 wt % |
| Ceteareth-25 | 2.5 wt % |
| Total | 100 wt % |

The above cream was tested for its effect against opportunistic *Candida albicans* on the skin of six volunteers. The pH of the cream was 5.0 to 6.0. Although topical candidiasis is normally very difficult to treat with antibiotics, it was found that the cream was effective, even after treatment of other diseases with antibiotics which often give *Candida albicans* a chance to become opportunistic. The treatment with the cream would normally lead to disappearance of the red spots on the skin after 3 to 7 days of treatment.

Thus a *Bulbine frutescens* extract has been made available wherein the active ingredient is plant-based, and the extract can be used in both the therapeutic and cosmetic fields for application to the skin and mucous membranes, can be formulated in a variety of dosage forms and offers a broad spectrum of effects. The efficacy is surprisingly high, even exceeding that of commercial products. Nevertheless there is a high tolerability in use, whereby at the same time the properties of the skin and mucous membranes are influenced in a positive sense.

What is claimed is:

1. A method of producing a *Bulbine frutescens* extract, comprising:
   (a) treating juice expressed from the leaves of *Bulbine frutescens* with hydrogen peroxide by combining the juice and hydrogen peroxide to form a solution;
   (b) thereafter, at least partially destroying the remaining hydrogen peroxide in the solution by adding an acid to the solution; and
   (c) adjusting the pH of the solution to 3.0 to 4.0 so as to produce a *Bulbine frutescens* extract.

2. The method of claim 1, further comprising the steps of washing *Bulbine frutescens* leaves, and expressing the washed leaves to yield the juice.

3. The method of claim 1, wherein the acid is chosen from the group consisting of: adipic acid, alginic acid, ascorbic acid, isoascorbic acid, aspartic acid, benzenesulfonic acid, succinic acid, 2-acetoxybenzoic acid, camphoric acid, camphorsulfonic acid, cinnamic acid, citric acid, digluconic acid, ethanesulfonic acid, glutamic acid, glycolic acid, heptanoic acid, hexanoic acid, fumaric acid, 2-hydroxyethanesulfonic acid, lactic acid, maleic acid, hydroxymaleic acid, malic acid, malonic acid, mandelic acid, pamoic acid, pectic acid, phenylacetic acid, 3-phenylpropionic acid, picric acid, pivalic acid, pyruvic acid, stearic acid, sulfanilic acid, tartaric acid, p-toluenesulfonic acid, and mixtures of two or more of the foregoing.

4. The method of claim 3, wherein the step of adjusting the pH of the solution comprises adding an acid to the solution, with the acid used for pH adjustment being the same as or different than the acid used to at least partially destroy remaining hydrogen peroxide.

5. The method of claim 4, wherein the acid used to at least partially destroy remaining hydrogen peroxide is selected from ascorbic acid, isoascorbic acid, and mixtures of ascorbic and isoascorbic acid, and the acid used for pH adjustment is citric acid monohydrate.

6. The method of claim 1, wherein the expressed juice is treated with 0.5 to 20 g of hydrogen peroxide per kg of juice.

7. The method of claim 6, wherein the expressed juice is treated with hydrogen peroxide for less than one hour.

8. The method of claim 1, wherein sufficient acid is added to reduce the peroxide value to less than 0.02 meq O/kg.

9. The method of claim 1, further comprising the step of combining the *Bulbine frutescens* extract with a pharmaceutically or cosmetically-acceptable preservative selected from the group consisting of: benzoic acid, sorbic acid, parabens, formic acid, acetic acid, propionic acid, salicylic acid, p-anisic acid, levulinic acid, water-soluble salts of any of the foregoing, glycerol and polyglycerol monoesters of caprylic acid, capric acid lauric esters, diols, and mixtures of two or more of the foregoing.

10. The method of claim 1, further comprising subjecting the *Bulbine frutescens* extract to further processing, wherein the further processing comprises at least one of: filtering, water evaporation, distillation, spray drying and freeze drying.

* * * * *

UNITED STATES PATENT AND TRADEMARK OFFICE
CERTIFICATE OF CORRECTION

PATENT NO. : 8,486,459 B2
APPLICATION NO. : 13/106175
DATED : July 16, 2013
INVENTOR(S) : Michel Colson It is certified that error appears in the above-identified patent and that said Letters Patent is hereby corrected as shown below:

On the title page of the patent insert the foreign priority claim:

--(30)   Foreign Application Priority Data

May 12, 2010   (DE) .............................................10 2010 028 960.4--

Signed and Sealed this
Twenty-fourth Day of September, 2013

Teresa Stanek Rea
*Deputy Director of the United States Patent and Trademark Office*